United States Patent
Bastia (12)

(10) Patent No.: US 8,808,177 B2
(45) Date of Patent: Aug. 19, 2014

(54) MEDICAL SURGICAL DEVICE FOR TREATING COLOPROCTOLOGICAL PATHOLOGIES

(75) Inventor: Filippo Bastia, Carpi (IT)

(73) Assignee: THD S.p.A., Correggio (IT)

( * ) Notice: Subject to any disclaimer, the term of this patent is extended or adjusted under 35 U.S.C. 154(b) by 1458 days.

(21) Appl. No.: 12/136,410

(22) Filed: Jun. 10, 2008

(65) Prior Publication Data

US 2009/0306481 A1 Dec. 10, 2009

(51) Int. Cl.
*A61B 1/32* (2006.01)
*A61B 1/31* (2006.01)
*A61B 1/07* (2006.01)

(52) U.S. Cl.
CPC .... *A61B 1/31* (2013.01); *A61B 1/07* (2013.01)
USPC .......................................... 600/245; 600/212

(58) Field of Classification Search
USPC ......... 600/178, 182, 184, 197, 199, 212, 241, 600/245, 249, 191; 362/32, 572
See application file for complete search history.

(56) References Cited

U.S. PATENT DOCUMENTS

| 2,482,971 A * | 9/1949 | Golson .................... 600/184 |
| 4,215,678 A | 8/1980 | Heine et al. |
| 4,566,439 A | 1/1986 | Burgin |
| 2006/0155169 A1 | 7/2006 | Bastia |

FOREIGN PATENT DOCUMENTS

| DE | 26 36 510 A1 | 2/1978 |
| GB | 551 146 A | 2/1943 |
| IT | 1 234 169 B | 5/1992 |
| WO | WO 01/43626 A1 | 6/2001 |
| WO | WO 0143626 A1 * | 6/2001 |
| WO | WO 01/60238 A1 | 8/2001 |
| WO | WO 01/74418 A2 | 10/2001 |
| WO | WO 2004/064624 A1 | 8/2004 |

* cited by examiner

*Primary Examiner* — Christian Sevilla
(74) *Attorney, Agent, or Firm* — Pearne & Gordon LLP

(57) ABSTRACT

A medical surgical device for coloproctological pathologies comprises a tubular body (2), provided with a first end (5), which can be inserted into the anal cavity, and a second end (6), opposite the first end (5) and connected to a handle (7) for maneuvering the tubular body (2) inside the anal cavity. A light source (8) for illuminating the inside of the tubular body (2) can be removably connected to the tubular body (2). Downstream of the light source (8) is located an entraining body (10) for entraining a portion of the light emitted by the light source (8) toward the inserting end (5). The entraining body (10) comprises a thickening (11) on the internal wall (3).

15 Claims, 2 Drawing Sheets

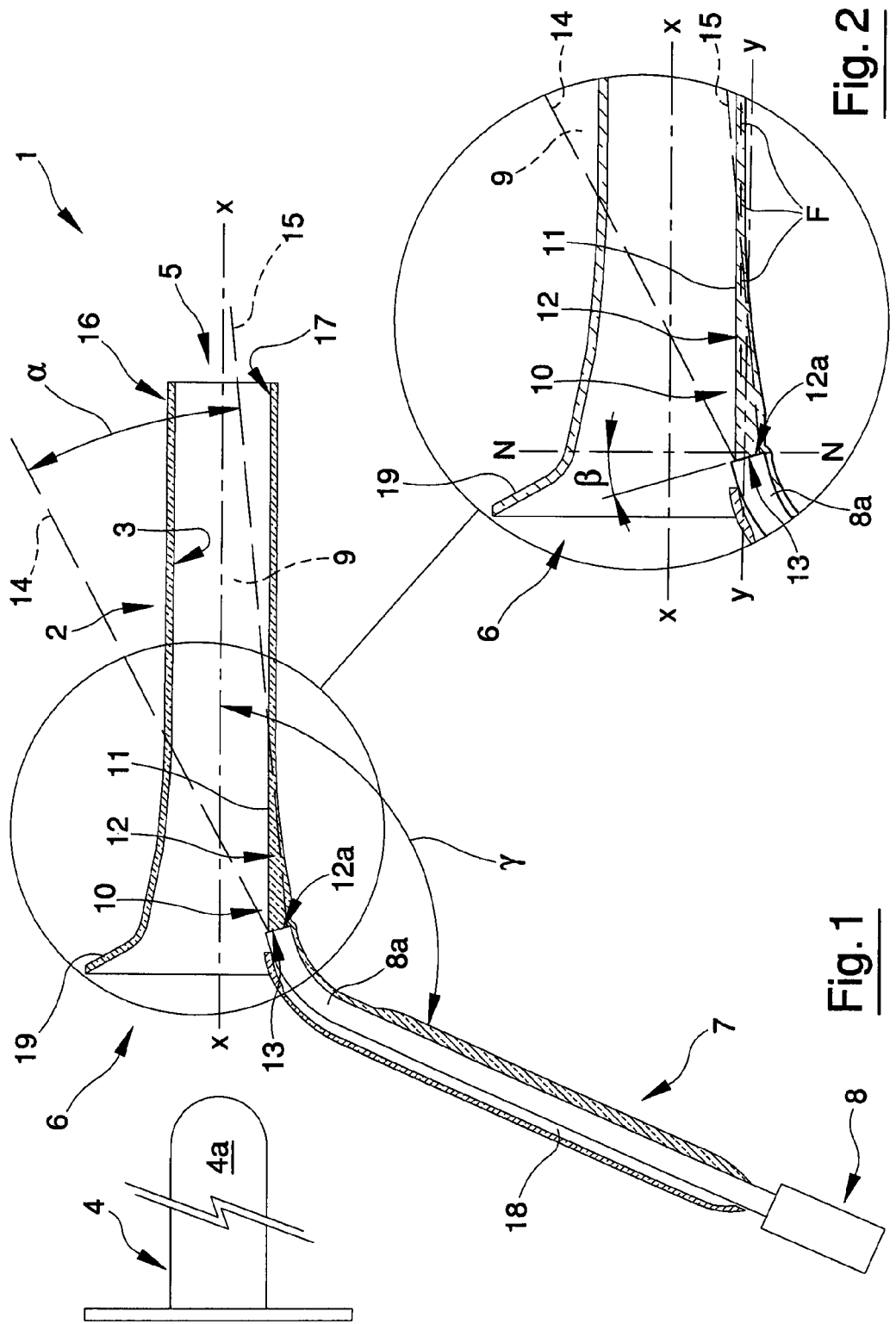

MEDICAL SURGICAL DEVICE FOR TREATING COLOPROCTOLOGICAL PATHOLOGIES

The present invention relates to a medical surgical device for coloproctological pathologies.

The device is applicable in the medical field both for the diagnosis and for the surgical treatment of coloproctological pathologies.

By coloproctological pathologies are meant all the pathologies which directly or indirectly concern the recto-intestinal tract of the human body, such as hemorrhoids, anal rhagades, internal mucous prolapses, anal fistulas, recto-vaginal fistulas, condylomas, rectoceles, anal cancers, anal fibrous polyps, hypertrophic anal papillomas, rectal prolapse, ulcerous rectocolitis, Crohn's disease, polyposis, colo-rectal tumours and/or the like. In order to aid diagnosis or treatment of the above mentioned pathologies, various prior art devices are known in the medical field, some of which have in common a tubular body with a handle which tubular body can be inserted into the anal cavity, also comprising a light source for illuminating the internal part of the tubular body when it is inserted.

The tubular body helps the dilatation of the anal canal side walls which are contractile as they consist of muscular tissue while the light source helps the visibility in the anal canal, which would otherwise be dark, so that the physician can make a diagnosis or surgically operate.

A main aim of the above-cited devices is to afford the surgeon the best possible visibility in the anal canal, while affording the largest possible maneuvering space for the surgical operations.

A partial solution might comprise a larger outer diameter of the tubular body.

The design conformation of the tubular bodies does not allow this solution, which although it would determine a wider field of visibility in the anal canal, would also cause dilatation stresses in the patient's sphincter.

There do in fact exist prior art tubular bodies with various different outer diameters, the smallest being used for purposes of diagnosis, while the largest, whose diameter is however not longer than 4.5 cm, are only for surgical uses, under anaesthesia.

In order to improve visibility internally of the tubular body, various different design conformations are used for optimising the light beam irradiated by the light source.

For example in the German patent application no. DE 2636510, entitled "Endoscope, in particular Rectoscope" a device is described which comprises a substantially cylindrical head, with a pair of concentric open tubes on an end thereof, the outer tube being transparent, the inner opaque, and on the opposite end means for focusing, movable on an end, facilitating magnification of the internal part of the anal cavity.

An optical fibre is inserted in the head transversally of the concentric tubes. The concentric tubes are in the terminal end, opposite the end connecting to the head; they are contained within a conical body which converges the light directly onto the cavity to be inspected.

The optical fibre, in collaboration with the structural conformation of the head, which is defined by two concentric cylindrical chambers, sends a light beam having a circular perimeter directly to the conical body.

The presence of the opaque body prevents a portion of the light beam from converging to the centre of the tubes and reflecting back to the surgeon's eye, thus dazzling him or her.

The above device, although it has improved visibility inside the tube, has some drawbacks.

Firstly the presence of the double concentric tubes, in which the outer tube must be distanced from the inner tube to form an interspace, involves the disadvantage of a limited space for the diagnosis as well as for operating.

For instance, If A is the maximum possible diameter of the device, the above-mentioned endoscope cannot have a diameter A for the inner tube and a larger diameter for the outer tube, but it will have an outer tube with a diameter A and an inner tube with a smaller diameter, with a consequently much smaller area of visibility.

The constructional conformation is also extremely expensive both because of the numerous elements used and due to the complex final assembly of the device.

It should also be specified that the device, due to the conical body generating a rise on the second outer tube, has some drawbacks during the extraction of the device from the anal cavity.

Still with reference to the conical body, it should also be specified that the device would not work without the conical body itself.

The conical body in fact converges the light beam toward the mucous tissue to be examined and/or to be surgically treated, at the centre of the terminal end and the mucous tissue is reflected internally of the inner opaque tube in a spreading direction from the terminal end to the connecting end.

Should the device be deprived of the conical body, the light beam would stay confined within the interspace between the tubes, and the opaque tube would prevent any penetration of the light beam into the device.

Another device is described in Italian patent application no. IT 1234169 entitled "A Single-use Device for Anoscopy and Proctoscopy".

The device shows a single tubular body provided with a transversal handle internally of which a pencil-type light source is housed.

The light source is entirely contained in the handle and terminates near the front portion of the tubular body, i.e. in the head thereof.

In this design circumstance the light source concentrates the illumination towards an area overlying the connection zone between the tube and the handle.

To facilitate illumination toward the centre of the device, a beam guide bar is arranged downstream of the light source.

The beam guide bar is arched and cylindrical, so as to deflect light from the direction parallel to the handle extension toward the internal part of the tubular body.

The presence of the light guide results in quite good luminosity inside the tube but the whole device has the drawback, as a result of reflection and refraction, of a low illuminating performance of the light source.

From a practical standpoint the present applicant has observed that, due to the conformation of the light guiding means, the terminal lower portion of the tubular body, opposite the connecting portion between the handle and the tube, comprises a shadowy area, a phenomenon which is accentuated along the axial development of the device.

A further disadvantage is that the above-mentioned device is expensive both because of the number of its components and because of the difficulty of assembly.

Assembling the device is indeed complex due to the separate manufacturing of the components and to the following installation of the means for guiding the light, which are also arranged in a position with difficult access.

An aim of the present invention is to produce a medical surgical device for coloproctological pathologies which is able to optimise the illuminating power of the light source.

A specific aim of the present invention is to provide a medical surgical device for coloproctological pathologies which offers a better illumination of the tubular lower portion.

A further aim of the invention is to provide a medical surgical device for coloproctological pathologies which is inexpensive with respect to both manufacturing and assembly.

A further aim of the invention is to provide a medical surgical device for coloproctological pathologies which internally affords a maximum exploitation of the space, without any additional body to reduce the maneuvering space for the surgical tools or which might generate shadowy areas.

The specified aims and still others are substantially achieved by a medical surgical device for coloproctological pathologies, according to the appended claims.

A preferred embodiment will now follow, by way of non-exclusive example, of a preferred embodiment of the medical surgical device for coloproctological pathologies of the invention, illustrated in the non-limiting appended figures, in which:

FIG. 1 is a cross section of a medical surgical device for coloproctological pathologies of the present invention;

FIG. 2 shows a detailed view in cross-section of a constructional detail of the device of FIG. 1;

Figure 3:
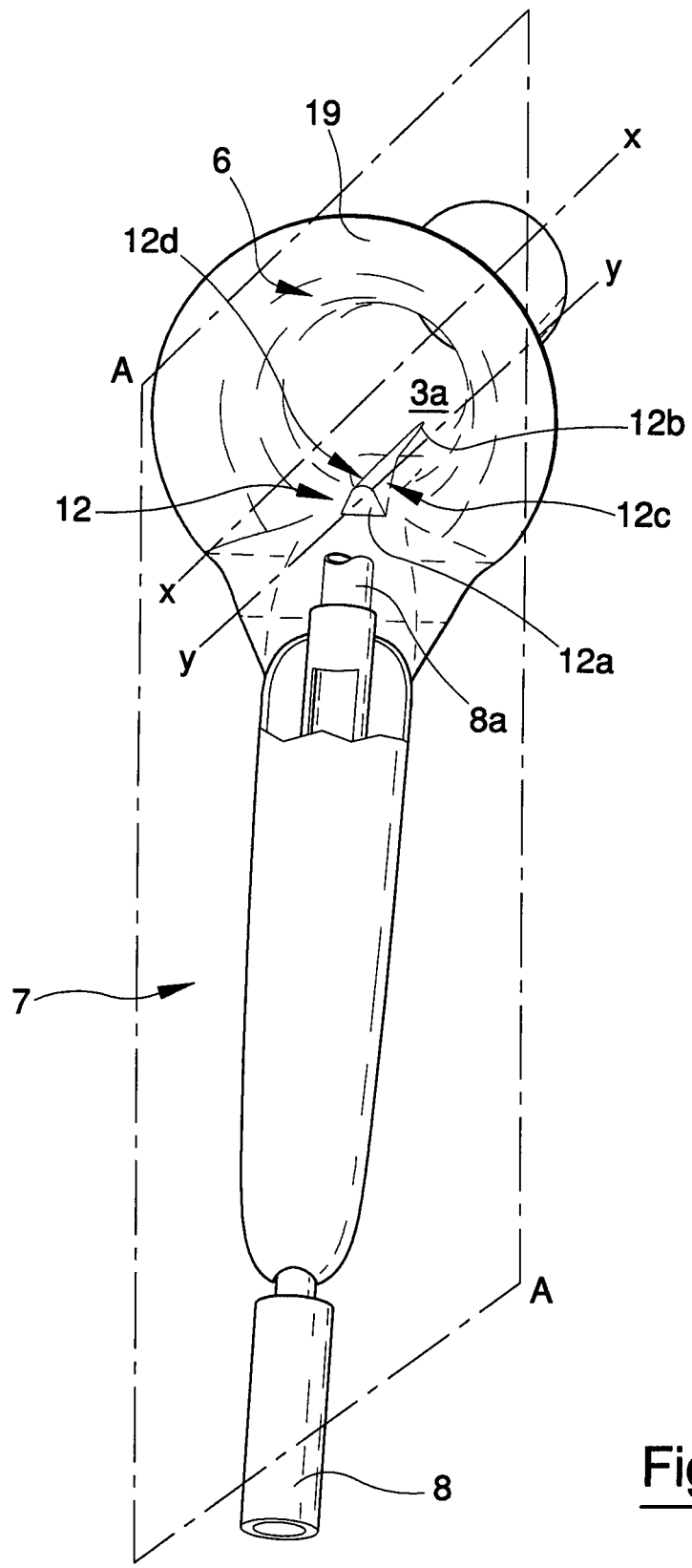
FIG. 3 shows a front perspective view of the device of FIG. 1.

With reference to the figures of the drawings, 1 denotes in its entirety a medical surgical device for coloproctological pathologies, preferably made of a plastic translucent material.

The device 1 is externally L shaped and exhibits a tubular body 2 and a handle 7.

The tubular body 2 develops prevalently along a longitudinal X-X axis, and its tubular shaped body internally defines an internal wall 3.

The internal wall 3 comprises an external limit edge 16 and a parallel internal limit edge 17, which together define the volume of the tubular body.

The tubular body 2, along its prevalently longitudinal extension, exhibits a first end 5, which can be inserted into the anal cavity, and a second end 6, opposite to the first and receiving a light beam 9 emitted by a light source 8 which can be connected to the tubular body 2.

Both ends 5, 6 are preferably open.

In order to facilitate insertion of the first end 5 into the anal cavity, the tubular body 2 is coupled to an introducing body 4.

The introducing body 4 is engaged in the tubular body 2, against its internal wall, and has a tapered distal end 4a which exits downstream of the tubular body 2 through the first end 5.

The second end 6 terminates in a flared portion 19 developing in an opposite direction to the inserting first end 5.

The flared portion 19, apart from facilitating the insertion of the inserting body 4 into the tubular body 2, also acts as a defensive barrier for the external tissue parts surrounding the anus.

A handle 7 is connected to the tubular body 2 at the second end 6 thereof, which handle 7 allows the tubular body 2 to be manoeuvred internally of the anal cavity.

By manoeuvrability, all the movements of the tubular body 2 along the longitudinal axis X-X are intended, i.e. the movements made during insertion and extraction of the tubular body 2, as well as all the rotations of the tubular body about the longitudinal axis, the movements made during the surgical operation or during the diagnosis of pathologies which present along the walls of the anal canal.

The tubular body 2 and the handle 7 form below them a γ angle comprised between 80 and 140 degrees, preferably 114 degrees.

The handle 7 internally comprises a housing seating 18.

A light source 8 can be installed inside the device 1 and an entraining body 10 is arranged downstream of the light source 8.

The light source 8 is arranged in proximity of the second end 6 and is removably connected to the tubular body 2.

As is visible in the appended figures the light source 8 is arranged in the is housing seating 18 of the handle 7.

The light source 8, used to illuminate the inside of the tubular body 2, produces a light beam 9 directed towards the first end 5.

In the preferred embodiment of the appended figures, the light source 8 consists of a arched body exhibiting a terminal portion 8a which is provided with an emitting surface 13 inferiorly located and resting on the internal wall 3.

The terminal portion 8a is connected to the internal limit edge 17 of the internal wall 3 of the tubular body 2.

As can be seen in FIGS. 1 and 2, the terminal portion 8a terminates tangentially to the internal limit edge 17 of the tubular body 2.

The emitting surface 13 irradiates the light beam 9.

The light beam is substantially cone-shaped, being defined by a upper generatrix 14 and a lower generatrix 15 forming between them an α angle comprised between 45 and 60 degrees.

The entraining body 10 is arranged inside the tubular body 2 to channel at least a part of the light beam 9 towards the first end 5.

The entraining body 10 comprises a thickening 11 of the internal wall 3 of the tubular body 2 for conveying a part of the light beam 9 and directing it through the internal wall 3.

As is shown in FIG. 2, F denotes the course of the portion of the light beam 9 which is intercepted and conveyed through the internal wall 3.

FIG. 3 shows that the thickening 11 is preferably located in a lower region 3a of the internal wall 3, close to the second end 6 of the tubular body 2.

In the tubular body 2, the thickening 11 defines a rise 12 exhibiting a linear development extending along a main y-y axis, which is substantially parallel to the longitudinal X-X axis of the tubular body 2.

The substantially parallel arrangement is due to the main y-y axis of the rise 12 being obliquely oriented.

More precisely, the y-y axis, with reference to its developing direction, i.e. from the second end 6 to the first end 5, diverges from the longitudinal axis X-X.

As is visible in FIG. 3, the main axis y-y of the rise 12 forms, together with the X-X longitudinal axis of the tubular body 2, an ideal A-A vertical plane.

In more detail, when the second end 6 of the tubular body 2 is frontal to the observer, the rise 12 is positioned in the middle of the lower concavity typical of the diameter cross-section of a tubular body 2.

The rise 12 has a front surface 12a, resting on the internal wall 3 of the tubular body 2 and arranged in proximity of the second end 6, and a back surface 12b arranged at a distance from the second end 6, sunk into the internal wall 3 of the tubular body.

As shown in the accompanying figures of the drawings, the rise 12 is substantially wedge-shaped.

In detail, the rise 12 has two sides 12c, 12d which taper going from the front surface 12a towards the back surface 12b.

In this configuration the back surface 12b is in fact an apex, sunk into the internal wall 3.

The front surface 12a rakes towards the opposite end 6 and forms a β angle of between 20 and 10 degrees, preferably 16 degrees, with respect to a plane perpendicular to the X-X axis.

The front surface 12a of the rise 12 also is substantially parallel to the emitting surface 13 of the light source 8.

The front surface 12a, which also acts as a striker ledge for the emitting surface 13 of the light source 8, has a smaller surface than the surface subtended from the emitting surface 13.

In this way, the light beam 9 emitted by the emitting surface 13 partly intersects the rise 12 and is partly directly irradiated into the tubular body 2.

A device of this kind offers important advantages. Firstly the thickening 11 of the internal wall 3 enables a part of the light beam 9 to be directed into the internal wall.

This characteristic generates a light beam that passes through the lower part of the tubular body 2, enabling the lower limit region of the first end 5 to be illuminated also.

Further, the surface of the front face 12a of the rise, though it does not intersect the entire portion of emitting surface 13 of the light source 8, does however illuminate the internal part of the tubular body 2, thanks to the known phenomena of direct irradiation, reflection and refraction.

It should be also observed that the geometric conformation of the rise means the device can be obtained directly by moulding, without any intermediate assembly.

The invention claimed is:

1. A medical surgical device for coloproctological pathologies comprising:
   a tubular body developing along a longitudinal axis, provided with an internal wall and exhibiting a first end, which can be inserted into an anal cavity, and a second end, opposite the first end and receiving a light beam emitted by a light source connectable to the tubular body;
   a handle connected to the tubular body at the second end thereof, for maneuvering the tubular body in the anal cavity;
   an entraining body, solidly constrained to the tubular body, located downstream of the light source to direct at least a part of the light beam towards the first end;
   wherein the entraining body comprises a thickening of the internal wall of the tubular body for entraining a part of the light beam and directing it towards the first end across the internal wall of the tubular body, the thickening comprising, inside the tubular body, a rise exhibiting a linear development along a main axis which is substantially parallel to the longitudinal axis of the tubular body, wherein the rise is substantially wedge-shaped and exhibits a front face resting on the internal wall of the tubular body and arranged in proximity of the second end thereof, and a back face sunk into the internal wall of the tubular body, the rise having a top, a portion of said top extending from the front face towards the back face, wherein the portion of the top which commences at the front face extends substantially parallel to the longitudinal axis of the tubular body.

2. The device of claim 1, wherein the thickening is located in a lower region of the internal wall, close to the second end of the tubular body.

3. The device of claim 1, wherein the main axis of the rise forms an ideal vertical plane with the longitudinal axis of the tubular body.

4. The device of claim 1, wherein the main axis develops in the developing direction from the second end to the first end, and diverges from the longitudinal axis.

5. The device of claim 1, wherein the rise has two sides tapered going in a direction towards the back face.

6. The device of claim 1, wherein the device further comprises a light source, located in proximity of the second end and removably connected to the tubular body, the light source comprising an arched body terminating in an emitting surface which develops a light beam and rests inferiorly on the internal wall of the tubular body.

7. The device of claim 1, wherein the internal wall is defined by an external limit edge and by an internal limit edge substantially parallel thereto, the limit edges defining the volume of the tubular body.

8. The device of claim 6, wherein the light source is defined by an arched body having a curved terminal portion which is connected to an internal limit edge of the internal wall of the tubular body.

9. The device of claim 1, wherein the front face acts as a striker ledge for an emitting surface of the light source.

10. The device of claim 1, wherein the front face is substantially parallel to an emitting surface of the light source.

11. The device of claim 1, wherein the front face is raked in a direction towards the second end of the tubular body and defines an angle of between 30 and 5 degrees with a plane perpendicular to the longitudinal axis.

12. The device of claim 1, wherein the front face has a smaller surface than a surface subtended from an emitting surface, in order to intersect a portion of the light beam emitted by the emitting surface.

13. The device of claim 1, wherein the handle exhibits a housing seating for accommodating the light source.

14. The device of claim 1, wherein the device also comprises an introducing body which can be engaged inside the tubular body, which introducing body is in contact with the internal wall and has a tapered distal end arranged downstream of the first end for facilitating insertion of the tubular body into the anal cavity.

15. The device of claim 1, wherein the front face is raked in a direction towards the second end of the tubular body and defines an angle of 16 degrees with a plane perpendicular to the longitudinal axis.

\* \* \* \* \*